United States Patent [19]

Lin

[11] 4,396,598

[45] Aug. 2, 1983

[54] TRIIODOISOPHTHALAMIDE X-RAY CONTRAST AGENT

[75] Inventor: Youlin Lin, Chesterfield, Mo.

[73] Assignee: Mallinckrodt, Inc., St. Louis, Mo.

[21] Appl. No.: 338,382

[22] Filed: Jan. 11, 1982

[51] Int. Cl.$^3$ .................... A61K 49/04; C07C 103/24
[52] U.S. Cl. ........................................ 424/5; 564/156
[58] Field of Search ............................ 424/5; 564/156

[56] References Cited

U.S. PATENT DOCUMENTS

| | | | |
|---|---|---|---|
| 4,001,323 | 1/1977 | Felder et al. | 424/5 X |
| 4,021,481 | 5/1977 | Almen et al. | 424/5 X |
| 4,250,113 | 2/1981 | Nordal et al. | 424/5 X |
| 4,278,654 | 7/1981 | Rakli et al. | 424/5 |

FOREIGN PATENT DOCUMENTS 26281  7/1980  European Pat. Off. .
2909439  9/1980  Fed. Rep. of Germany .

*Primary Examiner*—Bernard Helfin
*Attorney, Agent, or Firm*—R. J. Klostermann; L. N. Goodwin

[57] ABSTRACT

Novel X-ray contrast agents, i.e., N,N'-bis(2,3-dihydroxypropyl)-5-N-(2-hydroxyethyl)glycolamido-2,4,6-triiodoisophthalamide.

3 Claims, No Drawings

TRIIODOISOPHTHALAMIDE X-RAY CONTRAST AGENT

The present invention relates to new compounds, to radiological compositions containing such compounds and to the use of such radiological compositions.

Non-ionic contrast agents for intravascular and central nervous system visualization are complex molecules. As is known, the iodine in the molecule provides opacification to the X-rays. The remainder of the molecule provides the framework for transport of the iodine atoms. However, the structural arrangement of the molecule is important in providing stability, solubility and biological safety in various organs. A stable carbon-iodine bond is achieved in most compounds by attaching it to an aromatic nucleus. An enhanced degree of solubility as well as safety is conferred on the molecule by the addition of suitable solubilizing and detoxifying groups.

Several of the features that are desirable for intravascular and central nervous system non-ionic contrast agents are often incompatible so that all such agents represent compromises. In searching for the best compromise, the controlling factors are pharmacological inertness, i.e., in vivo safety, and high water solubility. Thus, the ideal intravascular or central nervous system non-ionic agent represents a compromise in an attempt to obtain the following criteria:
1. Maximum opacification to X-rays
2. Pharmacological inertness
3. High water solubility
4. Stability
5. Selective excretion
6. Low viscosity
7. Minimal osmotic effects An object of the present invention is to provide a non-ionic X-ray contrast agent. Another object of this invention is to provide a non-ionic X-ray contrast agent meeting substantially all the foregoing criteria.

This invention relates to N,N'-bis(2,3-dihydroxypropyl)-5-N-(2-hydroxyethyl)glycolamido-2,4,6-triiodoisophthalamide. N,N'-Bis(2,3-dihydroxypropyl)-5-N-(2-hydroxyethyl)glycolamido-2,4,6-triiodoisophthalamide is subject to a number of different types of isomerism as is explained below. The present invention extends to all isomers thereof. As used herein, the term N,N'-bis(2,3-dihydroxypropyl)-5-N-(2-hydroxyethyl)glycolamido-2,4,6-triiodoisophthalamide means N,N'-bis(2,3-dihydroxypropyl)-5-N-(2-hydroxyethyl)glycolamido-2,4,6-triiodoisophthalamide and all isomers thereof.

Exo and endo isomers exist due to restricted rotation of the N-CO bond caused by steric hindrance and the presence of the hydroxyethyl group. These isomers tend to equilibrate in solution but are sufficiently stable to be separated by thin layer chromatography.

In addition, there are two forms for each isomer due to restricted rotation of the N-(2-hydroxyethyl)-Ar bond. The compounds of the present invention also exist in racemic, optically active and meso forms.

Individual stereoisomers of the compounds of the invention can be obtained by conventional methods.

N,N'-Bis(2,3-dihydroxypropyl)-5-N-(2-hydroxyethyl)glycolamido-2,4,6-triiodoisophthalamide may be used as an X-ray contrast agent. The agent may be used in various radiographic procedures including those involving cardiography, coronary arteriography, aortography, cerebral and peripheral angiography, arthrography, intraveneous pyelography and urography as well as myelography. Mixtures of isomers of this invention may also be used as X-ray contrast agents.

A further feature of the present invention is a radiological composition containing N,N'-bis(2,3-dihydroxypropyl)-5-N-(2-hydroxyethyl)glycolamido-2,4,6-triiodoisophthalamide as an X-ray contrast agent together with a pharmaceutically acceptable radiological vehicle.

Pharmaceutically acceptable radiological vehicles include those that are suitable for injection such as aqueous buffer solutions, e.g., tris(hydroxymethyl)aminomethane (and its salts), phosphate, citrate, bicarbonate, etc., sterile water for injection, physiological saline, and balanced ionic solutions containing chloride and/or bicarbonate salts of normal blood plasma cations such as Ca, Na, K and Mg. Other buffer solutions are described in *Remington's Practice of Pharmacy, Eleventh Edition* for example on page 170. The vehicles may contain a chelating agent, e.g. a small amount, of ethylenediaminetetraacetic acid, the calcium disodium salt or other pharmaceutically acceptable chelating agents.

The concentration of N,N'-bis(2,3-dihydroxypropyl)-5-N-(2-hydroxyethyl)glycolamido-2,4,6-triiodoisophthalamide in the pharmaceutically acceptable vehicle, for example an aqueous medium, varies with the particular field of use. A sufficient amount is present to provide satisfactory X-ray visualization. For example, when using aqueous solutions for angiography the concentration of iodine is generally 140–400 mg/ml and the dose is 25–300 ml.

The radiological composition is administered so that the contrast agent remains in the living animal body for about 2 to 3 hours, although both shorter and longer residence periods are normally acceptable. N,N'-Bis(2,3-dihydroxypropyl)-5-N-(2-hydroxyethyl)-glycolamido-2,4,6-triiodoisophthalamide may thus be formulated for vascular visualization conveniently in vials or ampoules containing 10 to 500 ml. of an aqueous solution.

The radiological composition may be used in the usual way in X-ray procedures. For example, in the case of selective coronary arteriography, a sufficient amount of the radiological composition to provide adequate visualization, is injected into the coronary system and then the system is scanned with a suitable machine, for example a fluoroscope.

N,N'-Bis(2,3-dihydroxypropyl)-5-N-(2-hydroxyethyl)glycolamido-2,4,6-triiodoisophthalamide may be prepared in accordance with the procedures set out below. All temperature designations are in degrees centigrade.

EXAMPLE I

Preparation of
N,N'-Bis(2,3-dihydroxypropyl)-5-N-(2-hydroxyethyl)-glycolamido-2,4,6-triiodoisophthalamide (11)

A. Preparation of 5-Amino-2,4,6-triiodoisophthaloyl Chloride (2)

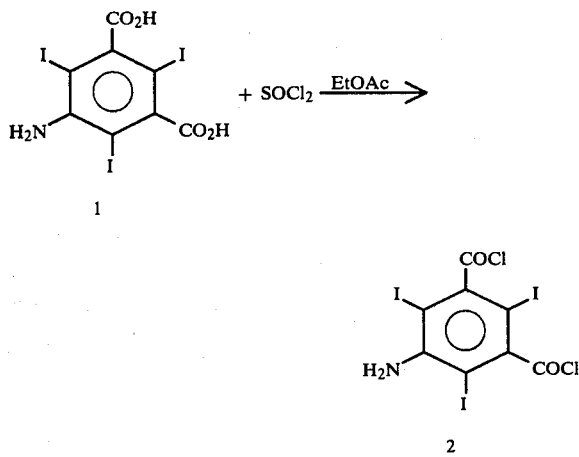

5-Amino-2,4,6-triiodoisophthalic acid (6.73 Kg, 12.04 mol) 1 was charged and EtOAc was added. $SOCl_2$ (5.73 Kg, 48.17 mol) was added to the slurry in one portion and the mixture was heated at reflux for 4 hours. After the reaction, 24.2 L of unreacted $SOCl_2$ and the solvent were distilled (64°-77°, 7 hrs. distillation time). The product started to precipitate when the reaction solution cooled to 55°; the slurry was stirred overnight, allowing it to cool to room temperature. The solids were collected, washed with cold EtOAc (5°, 3.8 L), suction-dried for 3 hours and air-dried at room temperature to give the desired product 2 (3.525 kg, 49.2% yield).

The filtrate (about 25 L) was distilled to a volume of 15 L and cooled to 2° overnight. The precipitated product was collected, washed with cold EtOAc (5°, 1.5 L), suction-dried and air-dried to give a second crop of the product 2 (0.83 kg, 11.6% yield). The two crops of the product were combined, 4.355 kg (60.8% yield). The product showed one spot by tlc analysis ($C_6H_5CH_3/CH_3OH$; 9/1).

B. Preparation of 5-Amino-N,N'-bis(2,3-dihydroxypropyl)-2,4,6-triiodoisophthalamide (4)

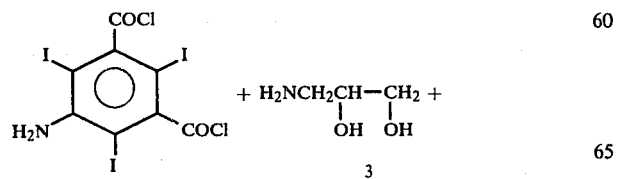

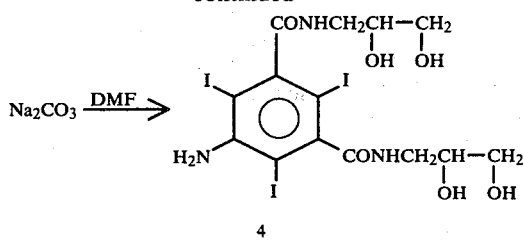

Pulverized 5-amino-2,4,6-triiodoisophthaloyl chloride 2 (4.35 Kg, 7.347 mol) was dissolved in DMF (6 L). The solution was cooled to 20° and $Na_2CO_3$ (2.33 Kg) was added; the temperature remained at 20°. To the reaction mixture was added, drop-wise, a solution of 3-amino-1,2-propanediol 3 (1.67 Kg, 22 mol) in 2.14 L of DMF with cooling (ice-bath) at 34°-35° over a period of 1.5 hour. After the addition, the reaction mixture was stirred at room temperature for 24 hours; the solid was filtered and washed with MeOH (3×500 ml). The filtrate and the MeOH wash were combined and evaporated under vacuum at 60°-63° (water bath) to give 4.5 L of a dark syrup. The warm syrup (50°-60°) was poured into a mixture of 45 L of water and 4 L of concentrated HCl with rapid stirring. The solution was stirred for 45 minutes, and evaporated under reduced pressure at 65°-70° (water-bath) to a volume of 28 L, washed with EtOAc (2×9 L) and further evaporated under reduced pressure at 65°-70° (water bath) to a volume of 12 L. The solution was diluted with 24 L of MeOH, seeded with an authentic sample of 4 (4-5 g) and stirred at room temperature for 2 days. Off-white solids precipitated during the stirring period. The solids were collected, washed with MeOH, suction-dried, and transferred to a tray and oven-dried at 70° for 24 hours to give the desired product 4 (2.582 Kg, 49.85% yield). The product showed one spot by tlc analysis (EtOAc/MeOH/AcOH; 10/5/1). LC purity: 98.5% (peak height) (μC18, $H_2O/CH_3CN$; 60/40, flow 1 mL/min, retention time 3 minutes).

C. Preparation of 5-Amino-N,N'-bis(2,3-diacetoxypropyl)2,4,6-triiodoisophthalamide (5)

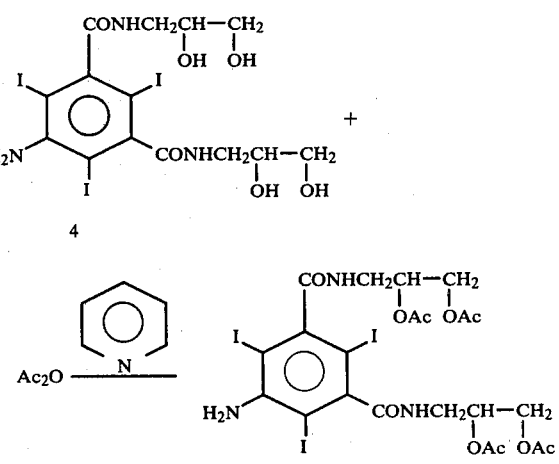

Compound 4 (2.58 Kg, 3.66 mol) was slurried in pyridine. Acetic anhydride (1.7 Kg, 16.65 mol) was added, drop-wise, to the slurry with stirring and cooling (ice-bath) over a period of 1.25 hours. The slurry temperature during this period was maintained at 33°–34°. After the addition the stirred slurry was allowed to cool to room temperature. During this time the slurry gradually became clear and the resulting solution was allowed to stir at room temperature for 17 hours.

The reaction solution (5.24 L) was diluted with EtOAc (10 L); ice water (7.32 L) was added and the mixture was stirred for 15 minutes. A mixture of ice water (7.32 L) and concentrated HCl (1.464 L) was added and the mixture was stirred for 45 minutes. The layers were separated (separation time 15 minutes) and the brown organic layer (bottom layer) was collected. The aqueous layer was extracted with EtOAc (2×5 L) and each time the organic layer (top layer) was collected. The organic layers were combined (25 L) and washed with the following solutions: 1. A mixture of water (3.66 L) and concentrated HCl (0.366 L); 2. A mixture of water (3.66 L) and concentrated HCl (0.18 L) and 3. 10% NaCl solution (4 L). The organic layer was then dried over anhydrous $Na_2SO_4$ (800 g) overnight. The solution was filtered and evaporated under reduced pressure at 60° (water bath) to give 5 as a yellow, glassy product. The product was then dried under vacuum at 60° for 13 hours, 3.21 kg (theory: 3.19 kg, >100% yield, due to the presence of HOAc).

The product showed one spot by tlc analysis (EtOAc/$CH_2Cl_2$; 30/20, Rf: 0.36); lc purity: 97–98%. ($\mu C_{18}$, $H_2O$/$CH_3CN$; 60/40, flow 1.0 mL/min, retention time 9.8 min); two minor peaks occurred before and one minor peak after the main peak.

D. Preparation of Acetoxyacetic Acid (Acetylglycolic Acid) (7)

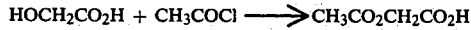

$$HOCH_2CO_2H + CH_3COCl \longrightarrow CH_3CO_2CH_2CO_2H$$
$$\quad 6 \qquad\qquad\qquad\qquad\qquad 7$$

Acetyl chloride (778.3 g, 9.91 mol) was slowly (30 min.) added to glycolic acid (493 g; 6.48 mol) with cooling and stirring. The temperature was kept at 15°–25°. After the addition was complete, the mixture was stirred at room temperature for 0.5 hour at which time a violent expulsion of HCl gas occurred causing the reaction to set up solid. Toluene (1 L) was added, and the mixture was heated to 70° in order to dissolve the solid. The solvent was removed under reduced pressure resulting in an oil to which toluene (2 L) was added. After the mixture was allowed to stand overnight, the solids were collected, washed with toluene (1 L) and air-dried to give 568.75 g (74.3%) of 7, m.p. 65°–66.5° (lit. 67°–70°). The pmr spectrum was consistent with the assigned structure.

E. Preparation of Acetoxyacetyl Chloride (8)

$$CH_3CO_2CH_2CO_2H + SOCl_2 \longrightarrow CH_3CO_2CH_2COCl$$
$$\qquad 7 \qquad\qquad\qquad\qquad\qquad 8$$

The acetoxyacetic acid (568.75 g, 4.82 mol) and thionyl chloride (759.19 g, 6.38 mol) were combined and heated with stirring at 65°–70° for 1 hour. The solution was then heated 1 hour at 70°–75° and lastly 1 hour at 77° (reflux). The thionyl chloride was removed under reduced pressure and the residue was vacuum distilled. The fraction boiling at 53°–60° (12–15 mm) was collected giving 85.6% of 8. The ir spectrum was consistent with the assigned structure.

F. Preparation of 5-Acetoxyacetamido-N,N'-Bis(2,3-diacetoxypropyl)-2,4,6-triiodoisophthalamide (9)

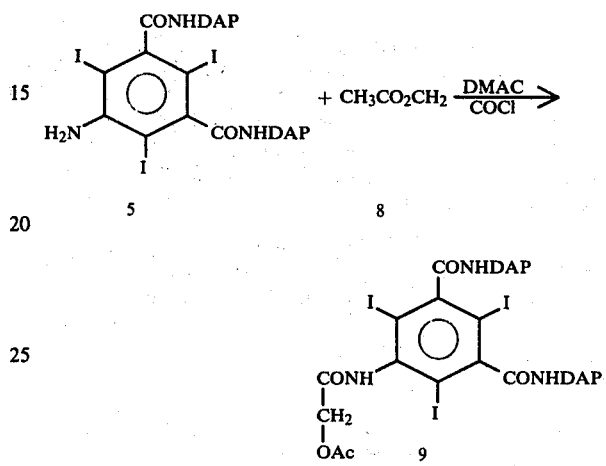

DAP = —$CH_2CHOAcCH_2OAc$

Compound 5 (349.32 g, 0.4 mol) and DMAC (1050 ml) were combined. The stirred mixture was cooled to 5°. The acid chloride (163.85 g, 1.2 mol) was added slowly keeping the temperature at 5°–10°. When the addition was complete the reaction mixture was allowed to warm to room temperature and was stirred for 16 hours. Water (36 ml) was added to the reaction mixture. The temperature rose to 48° and then began to fall. The mixture was added to water (5 L) which was extracted with ethyl acetate (4×1000 ml). The combined organic extracts were washed with 10% $NaHCO_3$ solution (2×1000 ml), water (1000 ml) dried over $Na_2SO_4$ and evaporated under reduced pressure to give 321.26 g (82.5%) of 9. The pmr spectrum was consistent with the assigned structure.

G. Preparation of N,N'-Bis(2,3-dihydroxypropyl)-5-glycolamido-2,4,6-triiodoisophthalamide (10)

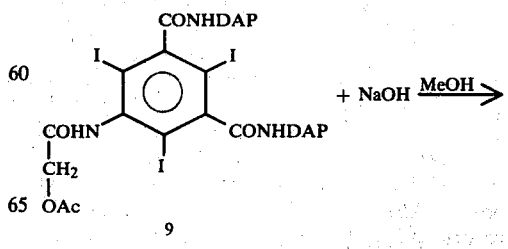
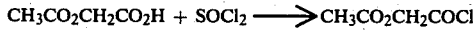

DAP = —$CH_2CHOAcCH_2OAc$

-continued

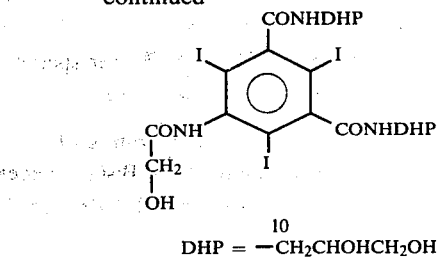

DHP = —CH₂CHOHCH₂OH

Compound 9 (321.26 g, 0.33 mol) and MeOH (1650 ml) were combined and stirred until all solids dissolved. To this solution was added 1 N NaOH (1650 ml, 1.65 mol). The mixture was stirred for 30 min; HCl (137.5 ml, 1.65 mol) was then added. The solution was evaporated under reduced pressure to give a residue which was carried on to the next step without purification.

H. Preparation of
N,N'-Bis(2,3-dihydroxylpropyl)-5-N-(2-hydroxyethyl)-glycolamido-2,4,6-triiodoisophthalamide (11)

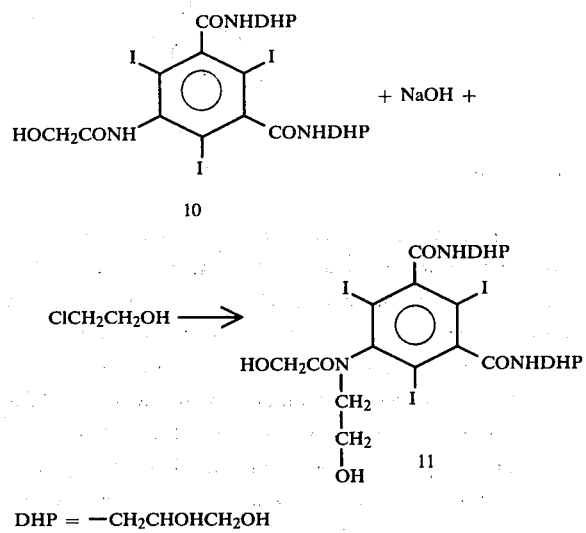

DHP = —CH₂CHOHCH₂OH

The residue 10 (251.82 g, 0.33 mol; assume theory) was mixed with 1 N NaOH (412 ml, 0.412 mol). The mixture was stirred at room temperature until all solids dissolved, then the solution was stirred for 1 hour. 2-Chloroethanol (40.25 g, 0.5 mol) was added and stirring was continued for three days. To the mixture was added 1 N NaOH (330 ml, 0.33 mol); and after the mixture was stirred for 1 hour, 2-chloroethanol (32.2 g, 0.4 mol) was added. After three more days, another portion of 1 N NaOH (150 ml, 0.15 mol) was added. After being stirred 1 hour, a final quantity of 2-chloroethanol (16.1 g, 0.2 mol) was added. The solution was stirred overnight and then was evaporated to dryness under reduced pressure. The residue was triturated with MeOH (1 L) for 1 hour. The precipitated solids were filtered off and the mother liquor was concentrated in vacuo. The crude product was purified by preparative liquid chromatography to give 127 g (47.7%) of 11; m.p. 186°–198°; tlc (CHCl₃/MeOH/HOAc, 70/30/2; Merck silica gel plate)-one spot (Rf-0.51); lc (H₂O/THF: 99.75/0.25; Hibar-II, Lichrosorb RP-18,10 μm, 10°) -two components (chromatographic purity: 97.3%); the ir and pmr spectra were consistent with the assigned structure Cal. for $C_{18}H_{24}I_3N_3O_9$; C: 26.78, H: 3.00; I: 47.17; N: 5.21 Found; C: 26.47; H: 3.23; I: 46.83; N: 5.12.

EXAMPLE II

RADIOGRAPHIC OBSERVATIONS

A male mouse (23 g) was anesthetized with sodium pentobarbital (40 mg/kg, i.p.; Nembutal ®, Abbott Laboratories). The N,N'-bis(2,3-dihydroxypropyl)-5-N-(2-hydroxyethyl)glycolamido-2,4,6-triiodoisophthalamide prepared by method of Example 1, was administered at a dose of 10,000 mg I/kg (40% I solution) via a lateral tail vein of the mouse at a rate of 1 ml/minute. Whole body radiographs in the ventrodorsal position were taken immediately and 5 minutes after administration with opacification of the liver and cardiovascular and renal excretory systems.

A pentobarbital-anesthetized male rat (234 g) received an intracisternal injection of 137 mg I/kg (40% I solution) of the N,N'-bis(2,3-dihydroxypropyl)-5-N-(2-hydroxyethyl)glycolamido-2,4,6-triiodoisophthalamide, prepared by method of Example 1. A lateral radiograph of the head and thorax, obtained immediately after administration, demonstrated good visualization of the cisterna magna, basal cisterns, and cervical subarachnoid space.

EXAMPLE III

The following pharmacological studies were conducted on N,N'-bis(2,3-dihydroxypropyl)-5-N-(2-hydroxyethyl)glycolamido-2,4,6-triiodoisophthalamide (PRODUCT), prepared by the method of Example 1.

1. Acute Intravenous Toxicity in Mice

A solution of the PRODUCT (40% I) was injected into the lateral tail vein of young adult male and female Swiss mice at a rate of 1 ml/min. Following injections, the animals were observed for immediate reactions and then daily throughout a seven day observation period. Lethality data were as follows:

| DOSE (mg I/kg) | DOSE (mg/kg) | NUMBER OF MORTALITIES/ NUMBER DOSED |
|---|---|---|
| 18,500 | 39,220 | 0/8 |
| 20,000 | 42,400 | 5/8 |
| 21,500 | 45,580 | 10/10 |

Thus the $LD_{50}$ value is probably about 20,000 mg I/kg.

2. Acute Intracisternal Toxicity in Rats

The technique described by Melartin, et al. (Invest. Radiol. 5: 13–21, 1970) was utilized to evaluate lethal effects of a solution of the PRODUCT after injection into cerebrospinal fluid at the cisterna magna. Young adult male Sprague Dawley rats were used. After dosing, the animals were housed individually and observed for immediate reactions and periodically for a two day observation period. The $LD_{50}$ value was calculated by the method of Litchfield and Wilcoxin (J. Pharmacol. Exp. Therap. 96: 99–113, 1949) with the following results:

| CONCENTRATION (mg I/kg) | $LD_{50}$/(95% Confidence Limits) | |
|---|---|---|
| | mg I/kg | mg/kg |
| 450 | 1,100 | 2,332 |

| CONCENTRATION | LD$_{50}$/(95% Confidence Limits) | |
|---|---|---|
| (mg I/kg) | mg I/kg | mg/kg |
| | (874–1,385) | (1,853–2,936) |

3. Acute Intracisternal Neurotoxicity in the Dog

Three dogs (2 male, 1 female) were briefly anesthetized with thiopental sodium (20 mg/kg, iv., Nembutal ®, Abbott Laboratories) and single doses of 314 (1 dog) or 320 Mg I/kg (2 dogs) of the PRODUCT (50% I solution) were administered into cerebrospinal fluid at the cisterna magna. The dogs were observed thereafter for neurotoxicity. The animals displayed moderate CNS depression but no signs of convulsive or preconvulsive behavior.

4. Intracoronary Cardiotoxicity in the Isolated Perfused Rabbit Heart

Four female New Zealand albino rabbits (3.4–4.3 kg) were employed for this study. Rabbits were sacrificed by cervical dislocation, the hearts excised and coronary perfusion was performed via the aortic root using an oxygenated physiological salt solution heated to 37° C. A solution of PRODUCT (37% I) was warmed to 37° C. and intracoronary bolus injections (4 ml) were made via a sidearm of the perfusion apparatus. The heart rate (HR), contractile force (CF), and electrocardiogram were recorded and results were as follows:

| | | Mean % Change from Control HR and CF - at Various Times after PRODUCT Administration | | | | | |
|---|---|---|---|---|---|---|---|
| DOSE (mg I/Heart) | | 0–15 sec | 15–30 sec | 1 min | 2 min | 4 min. | Arrythmias Observed |
| 1,480 | HR | −5 | 5 | 3 | 3 | −2 | None |
| | CF | 49 | 48 | 62 | 2 | −36 | |

What is claimed:

1. N,N'-Bis(2,3-dihydroxypropyl)-5-N-(2-hydroxyethyl)glycolamido-2,4,6-triiodoisophthalamide.

2. A radiological composition containing N,N'-bis(2,3-dihydroxypropyl)-5-N-(2-hydroxyethyl)-glycolamido-2,4,6-triiodoisophthalamide in a sufficient amount to provide satisfactory X-ray visualization together with a pharmaceutically acceptable radiological vehicle.

3. In a method for X-ray visualization wherein a radiological composition containing an X-ray contrast agent in a pharmaceutically acceptable radiological vehicle is injected in a sufficient amount to provide adequate visualization and thereafter X-ray visualization carried out, the improvement comprising or utilizing as the radiological composition a composition containing N,N'-bis(2,3-dihydroxypropyl)-5-N-(2-hydroxyethyl)glycolamido-2,4,6-triiodoisophthalamide in a sufficient amount to provide satisfactory X-ray visualization together with a pharmaceutically acceptable radiological vehicle.

* * * * *

UNITED STATES PATENT AND TRADEMARK OFFICE

CERTIFICATE EXTENDING PATENT TERM
UNDER 35 U.S.C. 156

Patent No.     : 4,396,598

Dated          : August 2, 1983

Inventor(s)    : YOULIN LIN

Patent Owner   : MALLINCKRODT, INC.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

815 DAYS with all rights pertaining thereto as provided by 35 USC 156 (b).

I have caused the seal of the Patent and Trademark Office to be affixed this 11th day of December 1989.

Jeffrey M. Samuels
Acting Commissioner of
   Patents and Trademarks